(12) United States Patent
Zhang et al.

(10) Patent No.: US 11,481,880 B2
(45) Date of Patent: Oct. 25, 2022

(54) POWER DOPPLER IMAGING SYSTEM AND METHOD WITH IMPROVED CLUTTER SUPPRESSION

(71) Applicant: KONINKLIJKE PHILIPS N.V., Eindhoven (NL)

(72) Inventors: Liang Zhang, Issaquah, WA (US); David Hope Simpson, Bothell, WA (US); Keith William Johnson, Lynwood, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 436 days.

(21) Appl. No.: 16/608,247

(22) PCT Filed: Apr. 17, 2018

(86) PCT No.: PCT/EP2018/059720
§ 371 (c)(1),
(2) Date: Oct. 25, 2019

(87) PCT Pub. No.: WO2018/197254
PCT Pub. Date: Nov. 1, 2018

(65) Prior Publication Data
US 2020/0184614 A1 Jun. 11, 2020

Related U.S. Application Data

(60) Provisional application No. 62/491,310, filed on Apr. 28, 2017.

(51) Int. Cl.
*G06T 5/20* (2006.01)
*A61B 8/06* (2006.01)
(Continued)

(52) U.S. Cl.
CPC .................. *G06T 5/20* (2013.01); *A61B 8/06* (2013.01); *A61B 8/12* (2013.01); *A61B 8/463* (2013.01);
(Continued)

(58) Field of Classification Search
None
See application file for complete search history.

(56) References Cited

U.S. PATENT DOCUMENTS 5,921,931 A 7/1999 O'Donnell et al.
6,181,810 B1 1/2001 Zhang et al.
(Continued)

FOREIGN PATENT DOCUMENTS

EP 1016875 A2 7/2000
JP H0339148 A 2/1991
(Continued)

OTHER PUBLICATIONS

PCT/EP2018/059720 Written Opinion and ISR, dated Jul. 10, 2018, 17 Page Document.

*Primary Examiner* — Leon Flores

(57) ABSTRACT

A method of power Doppler imaging may include receiving a plurality of temporally sequential frames of wall-filtered power Doppler signals, wherein the plurality of temporally sequential frames includes at least one previously adjusted output frame. The method may further include adjusting at least one of the plurality of temporally sequential frames to produce an adjusted output frame and generating a power Doppler image based, at least in part, on the adjusted output frame. The adjusting may involve filtering the plurality of temporally sequential frames to suppress the high spatial frequency and high temporal frequency content to produce the adjusted output frame.

15 Claims, 12 Drawing Sheets

(51) Int. Cl.
    *A61B 8/12*         (2006.01)
    *A61B 8/00*         (2006.01)
    *A61B 8/08*         (2006.01)
    *G06T 5/00*        (2006.01)
    *G06T 5/50*        (2006.01)

(52) U.S. Cl.
    CPC ............ *A61B 8/488* (2013.01); *A61B 8/5207* (2013.01); *G06T 5/002* (2013.01); *G06T 5/50* (2013.01); *G06T 2207/10132* (2013.01)

(56) References Cited

U.S. PATENT DOCUMENTS

| | | |
|---|---|---|
| 6,599,248 B1 | 7/2003 | Tamura |
| 6,663,567 B2 | 12/2003 | Ji et al. |
| 6,760,486 B1 * | 7/2004 | Chiao .................. G01S 15/8979 |
| | | 382/128 |
| 2009/0069675 A1 | 3/2009 | Srinivasan |
| 2011/0301470 A1 | 12/2011 | Sato et al. |
| 2013/0336560 A1 | 12/2013 | Wong |

FOREIGN PATENT DOCUMENTS

| | | |
|---|---|---|
| JP | H08168489 A | 7/1996 |
| JP | H10328180 A | 12/1998 |
| WO | 0173470 A1 | 10/2001 |

\* cited by examiner

POWER DOPPLER IMAGING SYSTEM AND METHOD WITH IMPROVED CLUTTER SUPPRESSION

CROSS-REFERENCE TO PRIOR APPLICATIONS

This application is the U.S. National Phase application under 35 U.S.C. § 371 of International Application No. PCT/EP2018/059720, filed on Apr. 17, 2018, which claims the benefit of U.S. Provisional Patent Application 62/491,310, filed on Apr. 28, 2017. These applications are hereby incorporated by reference herein.

This application relates to ultrasonic imaging and specifically to Doppler imaging systems and method which may be equipped with enhanced clutter suppression.

Existing ultrasound imaging system are operable to image in B-mode, producing grayscale images of the tissue or structures of the imaged anatomy, and are also typically operable to image in one or more Doppler modes to provide information about moving particles (e.g., blood flow). For conventional color Doppler imaging, the system transmits ultrasound pulses to the tissue and extracts blood flow information, such as phase and velocity information and power information, based on the Doppler effect. The Doppler signals are typically passed through a wall filter to suppress signals from moving tissue (also referred to as clutter). However conventional wall filters may not be able to adequately suppress tissue clutter, particularly when imaging low-velocity blood flow states and thus improved techniques for clutter suppression may be desired.

SUMMARY

A method of power Doppler imaging may include receiving a plurality of temporally sequential frames of wall-filtered power Doppler signals, wherein the plurality of temporally sequential frames includes at least one previously adjusted output frame. The method may further include adjusting at least one of the plurality of temporally sequential frames to produce an adjusted output frame and generating a power Doppler image based, at least in part, on the adjusted output frame. The adjusting may involve filtering the plurality of temporally sequential frames to identify low spatial frequency and high temporal frequency content and suppressing the low spatial frequency and high temporal frequency content to produce the adjusted output frame. In some embodiments, the filtering of the plurality of temporally sequential frames to identify low spatial frequency and high temporal frequency content may involve passing each of the plurality of temporally sequential frames through a spatial low-pass filter (e.g., a boxcar filter or another spatial low-pass filter) and through a temporal high-pass filter. The temporal high-pass filter may be implemented in accordance with any known technique such as by using a transfer function that is responsive to the change from frame to frame. Thereby, at the output of the filtering operation the low spatial frequency and high temporal frequency content will be identified and adjustment parameters (e.g., a gain adjustment, a blending coefficient, or other) may be computed for suppressing the low spatial frequency and high temporal frequency content from at least one of the temporally sequential frames (e.g., a current input frame). The adjustment parameter(s) may be applied to the at least one of the temporally sequential frames (e.g., a current input frame) to produce one or more adjusted frames and to subsequently produce power Doppler images based on the adjusted frame(s).

In some embodiments, the adjusting at least one of the plurality of temporally sequential frames may include filtering each of the plurality of temporally sequential frames to remove high spatial frequency content from each of the temporally sequential frames and produce filtered frames having relatively low spatial frequency content, determining the temporal responsiveness between the filtered frames for every spatial location in the frames, and adjusting the at least one of the plurality of temporally sequential frame based on the temporal responsiveness between the filtered frames. In some embodiments, the filtering each of the plurality of temporally sequential frames comprises passing each of the plurality of temporally sequential frames through a spatial low-pass filter. In some embodiments, the spatial low-pass filters may be a boxcar filter.

In some embodiments, the determining the temporal responsiveness between the filtered frames may include computing a change (for example, a percentage change or a fractional change, or simply a signal strength difference) in signal strength between the filtered frames for every pixel or voxel in the frames, and generating blending coefficients based on the computed changes in signal strength. In some examples, instead of using blending coefficients, the signal strength may be directly adjusted based on the computed change to produce the adjusted output frame. That is, adjusting of the input frame in the context of the present disclosure may be accomplished by adjusting a gain, by weighting, or one or more blending operations as further described below. The purpose of the adjustment may generally be to suppress the low spatial frequency and high temporal frequency content from the input frame and any suitable adjustment may be used to obtain that effect.

In some embodiments where blending is used, the generating of blending coefficients may include mapping the computed changes (e.g., percent, fractional, or simple difference in signal strength) for each pixel or voxel to respective blending coefficients using a transfer function. In some embodiments, the transfer function used may have a decay component and a growth component. In some embodiments, the method may further include generating second blending coefficients, for example based on a difference of the signal strength between the filtered frames at every pixel or voxel in the frames, and the adjusting of the input frame may be performed further using the second blending coefficients. As implied, the techniques described herein can be equally applicable to two-dimensional (2D) data sets, e.g., pixel-by-pixel processing of 2D image frames, or it may be applied to three-dimensional (3D) data set, such as by performing the clutter suppression on 3D data frames. In some embodiments, the steps of the process may be performed in real time, i.e., during the acquisition of one or more of the temporally sequential frames.

In further embodiments, the method may include blending the adjusted output frame with a corresponding echo frame to produce the power Doppler image. The adjusted output frame may include signal power information and the corresponding echo frame may include echo intensity information, and in some embodiments the blending of the adjusted output frame with the corresponding echo frame may involve computing at least one blending coefficient using at least one of the signal power information or the echo intensity information from the respective frame. Any of the methods described herein may be embodied in non-transitory computer-readable medium comprising executable instructions and which when executed cause a processor (e.g., a processor of an ultrasound imaging system) to perform the method embodied therein.

An ultrasound imaging system in accordance with some embodiments herein may be communicatively coupled to a source of ultrasound echoes for generating power Doppler images. The system may include a wall filter configured to produce wall filtered Doppler signals responsive to the ultrasound echoes, and at least one processor configured to process the wall filtered Doppler signals to produce power Doppler image data. The processor may be configured to receive temporally sequential frames of the wall filtered Doppler signals, wherein the two temporally sequential frames include at least one previously adjusted output frame, filter the temporally sequential frames to identify low spatial frequency and high temporal frequency content, suppress the low spatial frequency and high temporal frequency content to produce an adjusted output frame, and generate power Doppler image data based, at least in part, on the adjusted output frame.

In some embodiments of the system, the processor may include at least one spatial low-pass filter configured to remove high spatial frequency information from the temporally sequential frames to produce blurred frames and the processor may be further configured to generate one or more adjustment parameters based, at least in part, on the temporal responsiveness of the blurred frames. In some embodiments, the adjustment parameter may be simply an adjustment to the gain or it may be a blend parameter (e.g., blending coefficients, as further described below). In some embodiments, the processor may be configured to calculate a change in signal strength between the temporally sequential frames for all pixels or voxels in the respective frames, and wherein the one or more adjustment parameters include blending coefficients based at least in part on the based on the calculated changes in signal strength. The spatial low-pass filter may be a boxcar filter or another suitable low pass filter in some embodiments. In some embodiments, the processor may be configured to pass the calculated changes in signal strength through a transfer function to generate the blending coefficients, and wherein the transfer function comprises a decay component and a growth component. In some embodiments of the system, the blending coefficients may be first blending coefficients generated based on a fractional change in signal strength and the processor may be further configured to generate second blending coefficients based on a difference of the signal strength between the two temporally sequential frames, and adjust the current input frame further based on the second blending coefficients.

In some embodiments of the system, the processor may be configured to blend the adjusted output frame with a corresponding echo frame to produce the power Doppler image data. In some embodiments, the processor may be further configured to cause the display to display an ultrasound image including a B-mode image overlaid with the power Doppler image data. In further embodiments, the ultrasound system may include a transducer array configured to acquire the ultrasound echoes, and the processor may be operable to generate the power Doppler image data in real time while acquiring the ultrasound echoes.

DESCRIPTION

Figure 1:
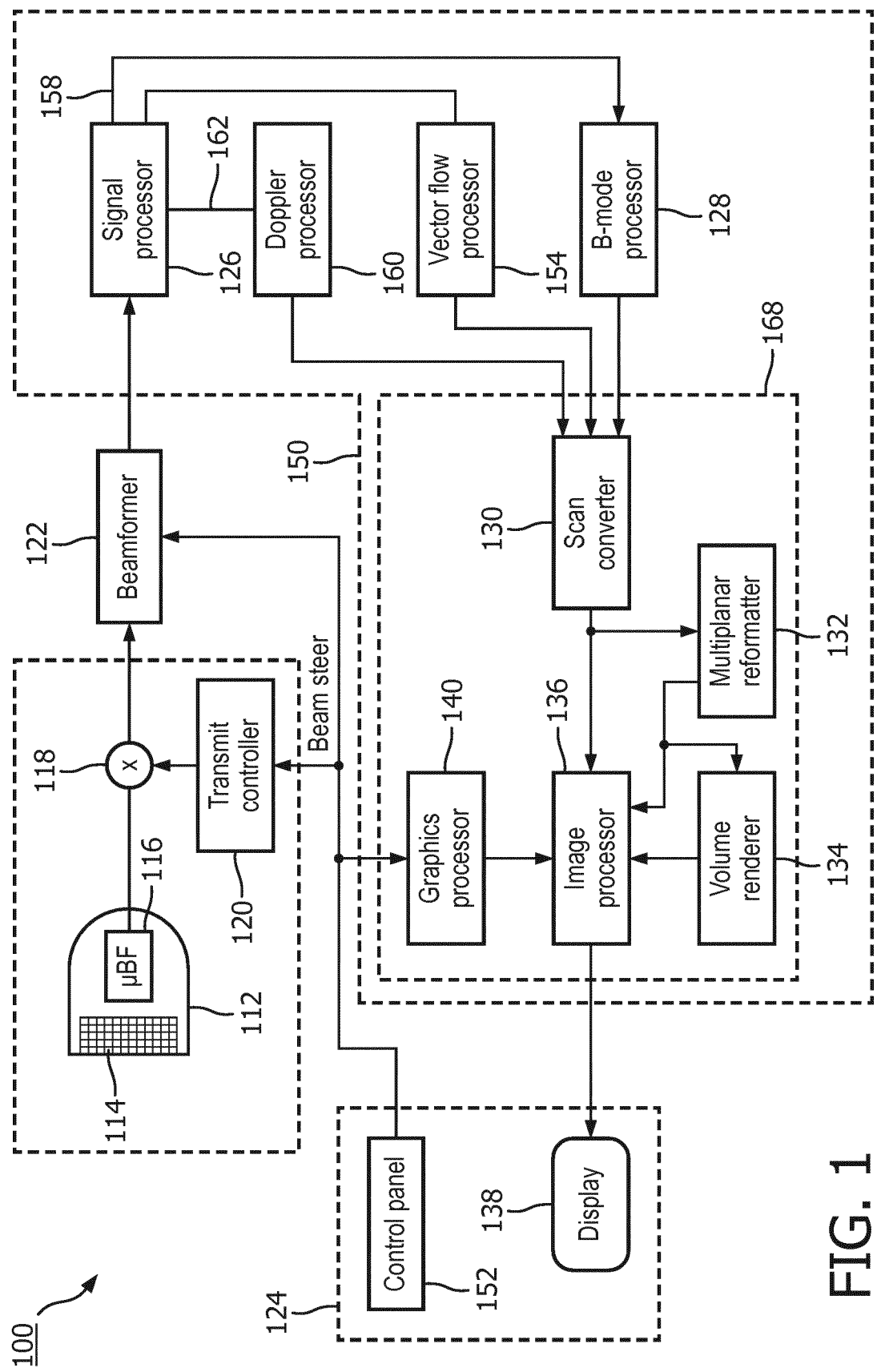
FIG. 1 is a block diagram of an ultrasound imaging system arranged in accordance with some embodiments of the present disclosure.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

A conventional ultrasound imaging system which is capable of perform Doppler imaging typically includes a wall filter in the Doppler signal path. The wall filter is a high-pass filter used to reduce or eliminate the high-amplitude, low-velocity echoes from vessel walls, often referred to as wall thump. The frequency cut-off of the filter may be configurable, and, is often set in the range of 50-1600 Hz. Many ultrasound imaging systems may also be configured to perform power Doppler imaging. In contrast to color (or colorflow) Doppler imaging which encodes estimates of the mean Doppler frequency shift at a particular position in color, power Doppler imaging is a technique that encodes the power of the Doppler signal in color. This parameter is fundamentally different from the mean frequency shift. While frequency of the signal is determined by the velocity of the tracked particles (i.e., red blood cells), the power of the Doppler signal depends on the amount of blood present.

Because power Doppler imaging may be used to provide an image of a different property of blood flow, power Doppler has shown several key advantages over color Doppler, including higher sensitivity to flow, better edge definition and depiction of continuity of flow. Power Doppler is therefore particularly useful for imaging superficial structures or small low flow vessels (e.g., capillary flow).

In Doppler imaging, flash artifacts often appear as a high intensity signal which appear rapidly in the temporal dimension and have a low spatial frequency. Conventional Doppler imaging relies on setting the wall filter in the Doppler signal path for flash artifact suppression. That is, to remove flash artifacts arising from tissue motion, conventional systems set the wall filter aggressively low and/or limit the power of the Doppler signal that passes the wall filter. The reason for this is that the strength of signals associated with tissue is typically much stronger than the strength of signals associated with blood flow. Specifically, when imaging low-velocity blood flow states with conventional systems, the wall filter is typically set low allowing for small Doppler shifted frequencies and their corresponding velocities caused by low-velocity blood flow to be seen and displayed. However, at low wall filter settings that may be suitable for imaging anatomy with low-flow states (e.g., relatively slower flow through the arterioles, veins, venules, or capillaries), Doppler shifts from tissue motion relative to the transducer are often times not readily filtered out and thus appear as a flash artifact. An improved system and method for flash artifact suppression for power Doppler imaging may be desirable.

This present disclosure may provide an improved solution to flash suppression in power Doppler imaging. In accordance with some examples herein, an additional flash suppression processing circuit is included in the power Doppler signal path to further reduce flash artifacts that arise when imaging anatomy with low-flow states. The flash suppression processing circuit (or simply flash suppression processor) may be configured to perform additional flash suppression (also referred to as clutter suppression) along the power Doppler signal path without affecting phase and velocity estimation within the Doppler processor. The inventors have recognized that when imaging flow in a low-flow state (e.g., venous flow or peripheral flow), the vessels associated with such low-flow states have a relatively lower resistive index and thus appear as a constant signal as opposed to the pulsatile signal typical of higher-flow states (e.g., arterial flow). Furthermore, signals produced from low-flow state blood flow are also typically associated with a relatively high spatial frequency. To that end, a system according to the present disclosure may include a spatiotemporal processing circuit which identifies, on a spatial regional basis, the change in intensity of a signal in two temporally sequential frames. As the change in signal intensity increases between the two temporally sequential frames, the signal is categorized as flash, and the persistence coefficient is altered adaptively in such a manner as to suppress the regional signal from the current frame and therefore suppress flash artifacts. The temporally sequential frames may be temporally consecutive frames, or they may be frames that are temporally sequential but spaced apart by one or more intermediate frames. Examples according to the present invention take advantage of the differences in spatial and temporal characteristics as shown in Table 1 below.

Flow information differs from tissue clutter in that flow information tends to be of high spatial frequency in the form of long, thin structures while tissue clutter tends to be of low spatial frequency which fills the near entirety of the ROI. It was also observed that flow information and tissue clutter behaved differently in the temporal dimension. Flow, particularly in the low-flow, small blood vessels (which are the vessels of particular interest) tended to have a low resistive index. This meant that flow generally remains constant throughout the cardiac cycle, much like venous flow. In contrast, 'flash' artifacts from tissue motion arising from the cardiac cycle have not been dampened to the extent that blood vessels have. Tissue cardiac motion is also not relegated to the small individual vessels but instead fills the entire tissue organ. As such, it is possible to roughly classify low-flow blood vessels and tissue clutter with the characteristics shown in Table 1.

TABLE 1

Difference in spatial and temporal characteristics between blood vessels and tissue.

| | Low-flow blood vessels | Tissue |
|---|---|---|
| Spatial characteristic | High-frequency | Low-frequency |
| Temporal characteristic | Low-frequency | High-frequency |

In accordance with principles of the present invention, spatial and temporal adaptive persistence is used to suppress flash artifacts. Persistence generally refers to the averaging of Doppler shift estimates from current and previous frames, and may interchangeably be referred to as frame averaging. The persistence controls are used to select the level of smoothing or frame averaging for the image display. High persistence is used for slow moving organs or objects of interest whereas low persistence is required for fast moving regions of interest such as the heart or fetal heart. The flash suppression process described herein may employ an infinite impulse response (IIR) style filter, which includes a feedback loop (e.g., uses the previously processed frame output from the filter as an input when processing a current frame). In this manner, the flash processing circuit described adaptively blends regions from the two frames to generate an output frame which contains flow information but with tissue flash components minimized. As such, tissue flash that spans greater than one input frame would not defeat the suppression process as compared to conventional temporal median filters that may be employed in existing power Doppler imaging systems, which would typically be defeated in such a scenario. The IIR filter described herein adaptively decides the contributions from two frames, which pixels to blend, and how much to blend.

Figure 2:
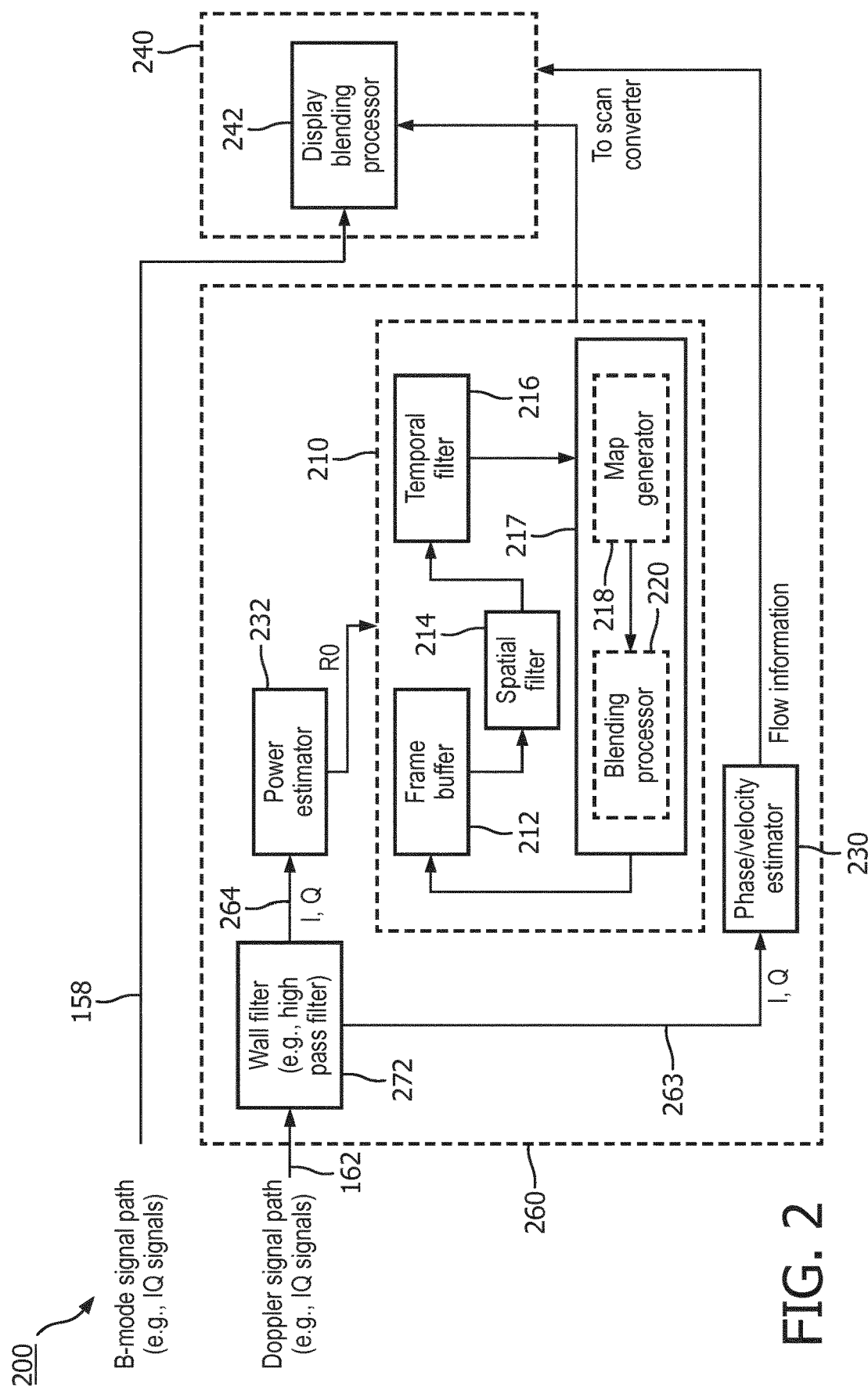
FIG. 2 is a block diagram of signal processing components of an ultrasound imaging system arranged in accordance with some embodiments of the present disclosure.

FIG. 2 shows a block diagram of a flash suppression processor in accordance with the present disclosure. The Flash suppression processor may be located on the Doppler signal path and operate on the spatial-temporal characteristics of the Doppler signal post wall-filter to produce an additionally de-cluttered output (also referred to as adjusted output) which may contain a flash corrected power signal. This output may be additionally, optionally blended with the echo signals (e.g., IQ demodulated signals) from the B-mode signal path to produce an enhanced power Doppler image, as will be further described. Before discussing components of an example flash suppression processor, an ultrasound imaging system which may include a flash suppression processor in accordance with embodiments of the present invention is described with reference to FIG. 1

FIG. 1 shows a block diagram of an ultrasound imaging system 100 constructed in accordance with the principles of the present disclosure. An ultrasound imaging system 100 according to the present disclosure may include a transducer array 114, which may be included in an ultrasound probe 112, for example an external probe or an internal probe such as an intravascular ultrasound (IVUS) catheter probe. In other embodiments, the transducer array 114 may be in the form of a flexible array configured to be conformally applied to a surface of subject to be imaged (e.g., patient). The transducer array 114 is configured to transmit ultrasound waves and receive echoes responsive to the ultrasound waves. A variety of transducer arrays may be used, e.g., linear arrays, curved arrays, or phased arrays. The transducer array 114, for example, can include a two dimensional array (as shown) of transducer elements capable of scanning in both elevation and azimuth dimensions for 2D and/or 3D imaging. As is generally known, the axial direction is the direction normal to the face of the array (in the case of a curved array the axial directions fan out), the azimuthal direction is defined generally by the longitudinal dimension of the array, and the elevation direction is transverse to the azimuthal direction. The transducer array 114 may be coupled to a microbeamformer 116, which may be located in the ultrasound probe 112, and which may control the transmission and reception of signals by the transducer elements in the array 114. In some embodiments, the microbeamformer 116 may control the transmission and reception of signals by active elements in the array 114 (e.g., an active subset of elements of the array that define the active aperture at any given time).

In some embodiments, the microbeamformer 116 may be coupled, e.g., by a probe cable or wirelessly, to a transmit/receive (T/R) switch 118, which switches between transmission and reception and protects the main beamformer 122 from high energy transmit signals. In some embodiments, for example in portable ultrasound systems, the T/R switch 118 and other elements in the system can be included in the ultrasound probe 112 rather than in the ultrasound system base, which may house the image processing electronics. An ultrasound system base typically includes software and hardware components including circuitry for signal processing and image data generation as well as executable instructions for providing a user interface.

The transmission of ultrasonic pulses from the transducer array 114 under control of the microbeamformer 116 is directed by the transmit controller 120, which may be coupled to the T/R switch 118 and the beamformer 122. In some embodiments, the probe 112 and beamformer may be coupled using a parallel data link to enable the simultaneous, parallel data transfer between the array and the base to enable the signal processing components to simultaneously receive data for multiple or all image lines in a field of view, such as during ultrafast imaging. The transmit controller 120 may also be coupled to the user interface 124 and receive input from the user's operation of a user controls. The user interface 124 may include one or more input devices such as a control panel 152, which may include one or more mechanical controls (e.g., buttons, encoders, etc.), touch sensitive controls (e.g., a trackpad, a touchscreen, or the like), and other known input devices.

Another function which may be controlled by the transmit controller 120 is the direction in which beams are steered. Beams may be steered straight ahead from (orthogonal to) the transducer array 114, or at different angles for a wider field of view. In some embodiments, the partially beamformed signals produced by the microbeamformer 116 may be coupled to a main beamformer 122 where partially beamformed signals from individual patches of transducer elements may be combined into a fully beamformed signal. The beamformed signals are coupled to processing circuitry 150, which may include one or more processors (e.g., a signal processor 126, a B-mode processor 128, a Doppler processor 160, a vector flow processor, and one or more image generation and processing components 168) configured to produce an ultrasound image from the beamformed signals (i.e., beamformed RF data).

The signal processor 126 may be configured to process the received beamformed RF data in various ways, such as bandpass filtering, decimation, I and Q component separation, and harmonic signal separation. The signal processor 126 may also perform additional signal enhancement such as speckle reduction, signal compounding, and noise elimination. The processed signals (also referred to as I and Q components or IQ signals) may be coupled to additional downstream signal processing circuits for image generation. The IQ signals may be coupled to a plurality of signal paths within the system, each of which may be associated with a specific arrangement of signal processing components suitable for generating different types of image data (e.g., B-mode image data, Doppler image data, vector flow image data). For example, the system may include a B-mode signal path 158 which couples the signals from the signal processor 126 to a B-mode processor 128 for producing B-mode image data. The B-mode processor can employ amplitude detection for the imaging of structures in the body.

The signals produced by the B-mode processor 128 may be coupled to a scan converter 130 and/or a multiplanar reformatter 132. The scan converter 130 may be configured to arrange the echo signals from the spatial relationship in which they were received to a desired image format. For instance, the scan converter 130 may arrange the echo signal into a two dimensional (2D) sector-shaped format, or a pyramidal or otherwise shaped three dimensional (3D) format. The multiplanar reformatter 132 can convert echoes which are received from points in a common plane in a volumetric region of the body into an ultrasonic image (e.g., a B-mode image) of that plane, for example as described in U.S. Pat. No. 6,443,896 (Detmer). A volume renderer 134 may generate an image of the 3D dataset as viewed from a given reference point, e.g., as described in U.S. Pat. No. 6,530,885 (Entrekin et al.).

In some embodiments, the system may include a Doppler signal path 162 which couples the output from the signal processor 126 to a Doppler processor 160. The Doppler processor 160 may be configured to estimate the Doppler shift and generate Doppler image data. The Doppler image data may include color data which is then overlaid with B-mode (i.e. grayscale) image data for display. The Doppler processor 160 may be configured to filter out unwanted signals (i.e., noise or clutter associated with non-moving tissue), for example using a wall filter. The Doppler processor 160 may be further configured to estimate velocity and power in accordance with known techniques. For example, the Doppler processor may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. In some examples, the velocity and power estimates may undergo further threshold detection to further reduce noise, as well as segmentation and post-processing such as filling and smoothing. The velocity and power estimates may then be mapped to a desired range of display colors in accordance with a color map. The color data, also referred to as Doppler image data, may then be coupled to the scan converter 130, where the Doppler image data may be converted to the desired image format and overlaid on the B-mode image of the tissue structure to form a color Doppler or a power Doppler image.

In yet further examples, the system may include additional signal processing paths, such as a vector flow processing path, which couples the data from the signal processor 126 to a vector flow processor 154. The vector flow processor may be configured to extract angle-independent estimates of the velocity of flow through the imaged volume and map the velocity information into a graphical representation (e.g., streamline or pathlet-based visualization) of the velocity vector field. In some example, the vector flow processor may be configured to estimate axial and lateral components of the flow velocity, and in examples where the system is operable to image a three-dimensional (3D) region of interest (ROI), to also estimate the elevational components of the flow velocity for generating 2D or 3D velocity vector fields or maps. As with the B-mode and Doppler processors, vector flow imaging data may be coupled to the scan converter, multiplanar reformatter and/or volume renderer for combining (e.g., overlaying) the vector flow imaging data with, e.g., B-mode image data to produce an overlay ultrasound image displaying angle-independent velocity information concurrently with the associated tissue structure.

Output (e.g., B-mode images, Doppler images, vector flow images) from the scan converter 130, the multiplanar reformatter 132, and/or the volume renderer 134 may be coupled to an image processor 136 for further enhancement, buffering and temporary storage before being displayed on an image display 138. A graphics processor 140 may generate graphic overlays for display with the images. These graphic overlays can contain, e.g., standard identifying information such as patient name, date and time of the image, imaging parameters, and the like. For these purposes the graphics processor may be configured to receive input from the user interface 124, such as a typed patient name or other annotations. In some embodiments, one or more functions of at least one of the graphics processor, image processor, volume renderer, and multiplanar reformatter may be combined into an integrated image processing circuitry (the operations of which may be divided among multiple processor operating in parallel) rather than the specific functions described with reference to each of these components being performed by a discrete processing unit. Furthermore, while processing of the echo signals, e.g., for purposes of generating B-mode images or Doppler images are discussed with reference to a B-mode processor and a Doppler processor, it will be understood that the functions of these processors may be integrated into a single processor. Referring now also to FIG. 2, a flash suppression processor 210 in accordance with some embodiments of the present disclosure.

FIG. 2 shows a block diagram of at least part of the processing circuitry along the Doppler and B-mode signal paths 162 and 158, respectively. Along the Doppler signal path 162, signals (e.g., IQ signals received from the signal processor 126) are coupled to a Doppler processor 260, which may initially pass the received signals through a wall filter (e.g., a high-pass filter) to remove signals associated with strong slower motion such as cardiac cycle tissue motion. The wall filtered signals may then be provided, e.g., along parallel signal paths (e.g., 263 and 264), to a phase/velocity estimator 230 and to a power estimator 232, which are configured to obtain flow information and power information, respectively, from the Doppler signals. Phase/velocity estimate and power estimates may be obtained in accordance with any of the techniques described above with reference to FIG. 1 or any other known technique.

As shown in FIG. 2, the Doppler processor 260 may include a flash suppression processor 210 which is arranged to perform additional clutter suppression on the post wall filtered power Doppler signals, e.g., without affecting the Doppler signals that are used for phase/velocity estimates. An example flash suppression processor 210 may include one or more buffers and one or more signal processing components including a spatial characteristic processing unit, a temporal characteristic processing unit, and a frame adjustment unit, which may, in some embodiments, be implemented by a blending map generation unit and a blending unit. The flash suppression unit 210 receives frames of wall filtered Doppler signals, and specifically the power component of the Doppler signals. The frames may be temporarily stored in a buffer (e.g., frame buffer 212) until used by the signal processing components of the flash suppression processor 210. The frames are temporally and spatially processed such as to identify low spatial frequency and high temporal frequency content, and one or more of the input frames are adjusted (e.g., blended or otherwise adjusted to suppress the low spatial frequency and high temporal frequency content) to produce an adjusted output frame which may then be used for generating an enhanced power Doppler image. While the spatial and temporal filtering is described in a given sequence in this example, it will be understood that the order of the processing steps may be changed (e.g., reversed, such that the temporal filtering is performed before the spatial filtering).

The spatial characteristic processing unit may be configured to receive the wall filtered Doppler frames and spatially filter each frame to identify low spatial frequency information, while removing high spatial frequency content. The low-spatial frequency content, which may be indicative of tissue as shown in Table 1, will them be filtered further to identify regions (e.g., pixels or voxels) with content that varies in the temporal dimension so as to identify tissue motion for subsequent suppression. In some examples, the spatial characteristic processing unit may be implemented using a spatial low-pass filter 214 (also referred to as clutter filter), which in some examples may be a boxcar filter. For example, a 2D boxcar filter using a 2D sinc Fourier transform may be used to filter out the high spatial frequency information and pass the low spatial frequency information along the signal path for further processing. As each frame is processed by the spatial filter 214, a blurred frame may be produced and the set of input frames may then be coupled to the temporal characteristic processing unit for further processing. Other smoothing or bluffing filters may be used in other examples.

The temporal characteristic processing unit may be configured to receive two or more temporally sequential (for example, temporally consecutive) frames and identify regions with high temporal frequency information (i.e., regions or pixels rapidly changing in the temporal domain), which may be indicative of flash. The temporal characteristic processing unit may be provided by a temporal high-pass filter configured to identify frame content that varies from frame to frame, for example. In a specific embodiment, discussed further below, the temporal responsiveness between frames may be characterized by calculating the change in signal strength (e.g., by calculating a percent change, a fractional change, or difference between the signal strength in the two or more blurred frames). Once frame content with low spatial frequency and high temporal frequency has been identified, this content can then be further suppressed by adjusting at least one of the input frames (e.g., by blending, gain adjustments, or other) to produce an adjusted output frame. In some embodiments, the frame adjustment (e.g., suppression of low spatial frequency and high temporal frequency content) may be made by a blending operation, as will be described in further detail below. In such embodiments, the frame adjustment unit 217 may be implemented using a blending map generation unit 218 and a blending processor 220. The output from the filtering steps may be coupled to the blending map generation unit, also referred to as map generator 218.

The blending map generation unit (i.e., map generator 218) may be configured to generate a pixel by pixel map of blending or persistence coefficient values (e.g., an alpha blending map and/or a beta blending map). The blending map generation unit 218 may pass the signal strength change values received from the temporal characteristic processing unit through a transfer function to map the signal strength change values to a blending or persistence coefficient value (e.g., ranging from 0-1) for each pixel in the frame. A variety of transfer functions, for example a linear parabolic transfer function, may be used for generating the coefficient map. The coefficient values may then be passed to a blending unit to produce a compensated or flash suppressed output. In some embodiments, a plurality of blending maps may be produced to further enhance the blending process, as will be described e.g., with reference to FIG. 3B. The blending map(s) generated by the blending map generation unit (i.e., map generator 218) are coupled to a blending unit, which is configured to provide the adjusted (or flash suppressed) output data. In the output from processor 210, low spatial frequency and high temporal frequency content (e.g., consistent with tissue motion, as per Table 1) has been further suppressed and thus resulting power Doppler images generated using the adjusted output data may be of higher quality than would have been previously possible (e.g., simply using the data as filtered by a conventional wall filter).

The adjusted output from the flash suppression processor 210 may be coupled to further downstream image processing (e.g., a scan converter, image and/or graphics processors, further blending processors, etc.) for generating a power Doppler image. In some embodiments, the power Doppler data output from flash suppression processor 210 may be blended for display with the corresponding echo information (e.g., a B-mode image frame received from the B-mode signal path 158) in a downstream blending processor (also referred to as display blending processor 242), the functionality of which will be further described, for example with reference to FIGS. 8A-8C. The functionality of the display blending processor 242 may be incorporated into the scan converter 240 or another one of the image generation and processing components of the ultrasound system (e.g., processor 168 of system 100).

Figure 3A:
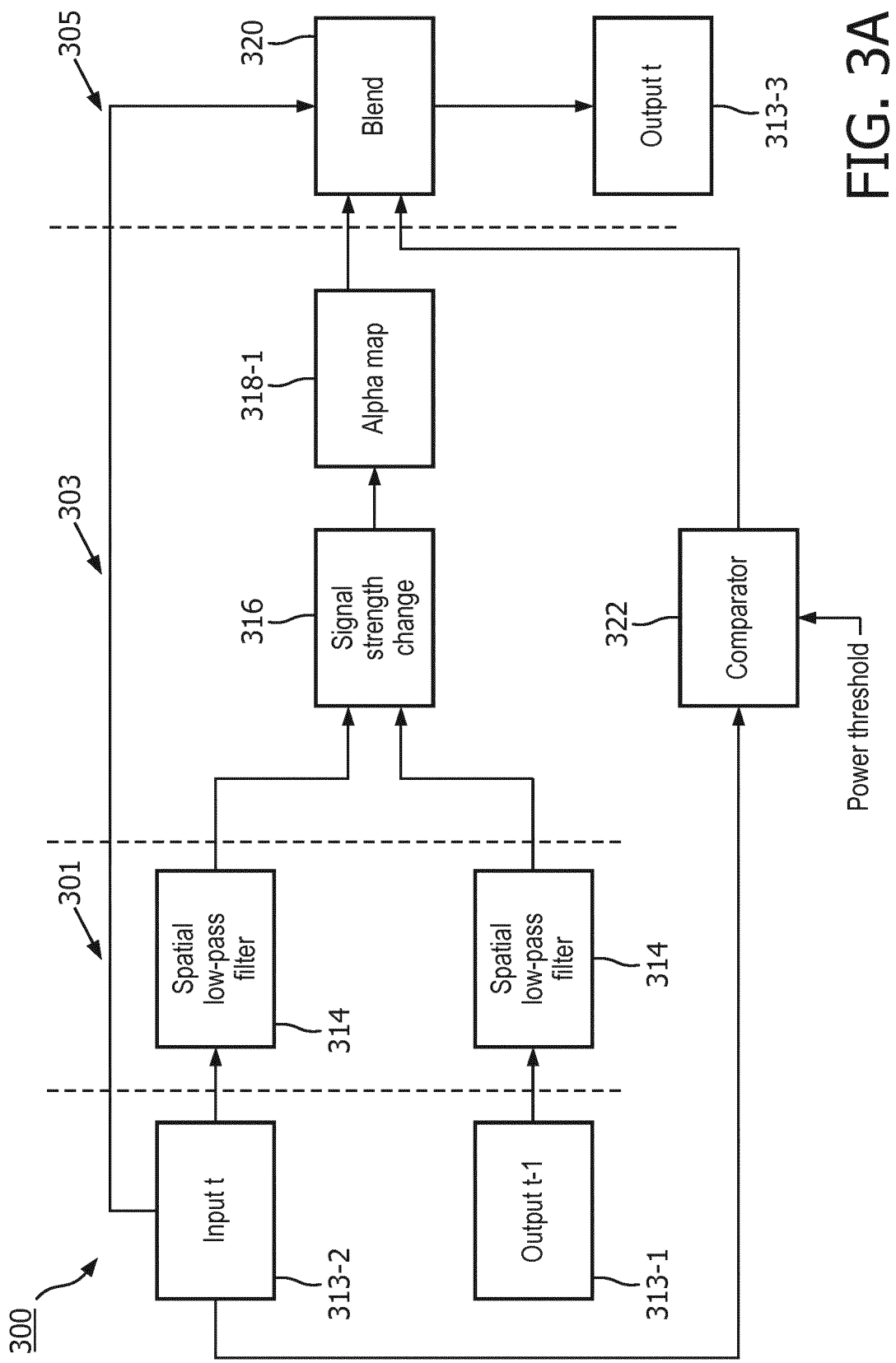
FIG. 3A is an example of a flash suppression processor in accordance with some embodiments of the present disclosure.
Figure 3B:
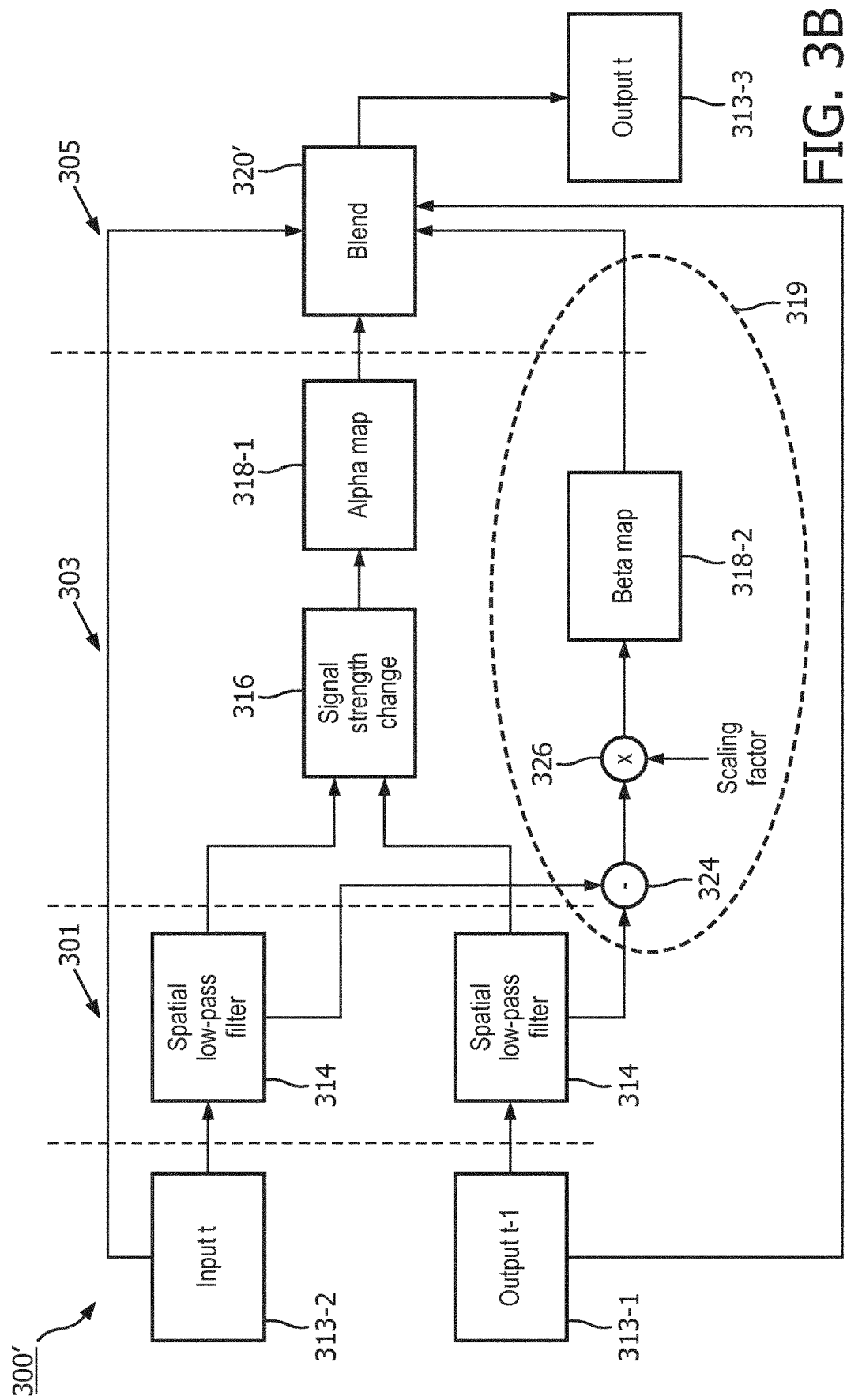
FIG. 3B is another example of a flash suppression processor in accordance with some embodiments of the present disclosure.

FIGS. 3A and 3B show examples of flash suppression units 300 and 300' in accordance with embodiments of the present invention. As described herein, the flash suppression units 300 and 300' include a spatial characteristic processing stage 301, a temporal characteristic processing stage 303, and a blending stage 305. In the spatial characteristic processing stage 301, spatial low pass filters 314 may be used to remove high spatial frequency content, while preserving the low spatial frequency content, of each of the temporally sequential frames 313-1 and 313-2 (e.g., labeled as output t−1 and input t, respectively, in the illustrated example). In the temporal characteristic processing stage 303, one or more regions (e.g., one or more pixels in the frame) that include high temporal frequency content may be identified and at least one map which captures a temporal change in the signal is generated.

The operation of flash suppression units 300 and 300' is now described in further detail. At an example time t, the spatial low-pass filter receives the current frame 313-2, denoted by input t, and the previous output frame 313-1, denoted by output t−1, as inputs. Each of the frames is filtered by a low-pass filter 314 to remove their high spatial frequency content, while preserving low spatial frequency content. In this manner, high spatial frequency content associated with low-flow blood vessels is suppressed in accordance with the observations in Table 1. The low-pass filters 314 output blurred frames Blur t, labeled as 315-2 and Blur t−1, labeled as 315-1. In some embodiments, the low pass filter 314 may be implemented using a 2D Boxcar filter. The 2D boxcar filter, the filter size of which may be determined through optimization, is a relatively simple to implement blurring kernel and is thus one example of a filter that may be used. Other spatial low-pass filters may be used in other embodiments.

Next, a change in signal strength is computed for every spatial location in the blurred frames Blur t and Blur t−1, as shown at block 316. The computed change is used to provide information on the temporal characteristics (e.g., temporal responsiveness) of the signals at each spatial location. The change in signal strength may be computed by: FractionalChange=(New−Old)/(New+Old), where the New corresponds to the signal strength of the current input (e.g., input t) and Old corresponds to the signal strength of the previous input (e.g., output t−1). If New and Old are both large, then FractionalChange would tend to be small due to the denominator term. Compared to that, if New and Old are small, than the FractionalChange will tend to be larger for the same absolute difference between New and Old. For example, if New=10 and Old=5, then FractionalChange=0.333. It is noted that in some examples, the fractional change definition may be FractionalChange*100, however, in this specific example the multiplication by 100 is excluded. For the same numerator, if New=6 and Old=1, then FractionalChange=0.714. This bias for absolute values of New and Old may function well for discriminating between flow and tissue because post wall-filtered flow signal tends to be large and relatively constant, while tissue flash tends to be strong in one frame but weak in another frame with overall smaller values. FractionalChange tends to be larger for tissue flash compared to flow for the same absolute difference between New and Old.

The computed change in signal strength may then be fed into a transfer function to generate a first blending map (e.g., an Alpha map 318-1), which may be used by the blending processor 320 to produce output 313-3. In this manner, large changes in signal strength may be penalized heavily in the Alpha map 318-1, which may serve to further discriminate between tissue and flow information according to Table 1. Since tissue flash arising from cardiac motion is of low spatial frequency, removing low spatial frequency changes in signal intensity will further suppress flash in the output image.

Figure 4:
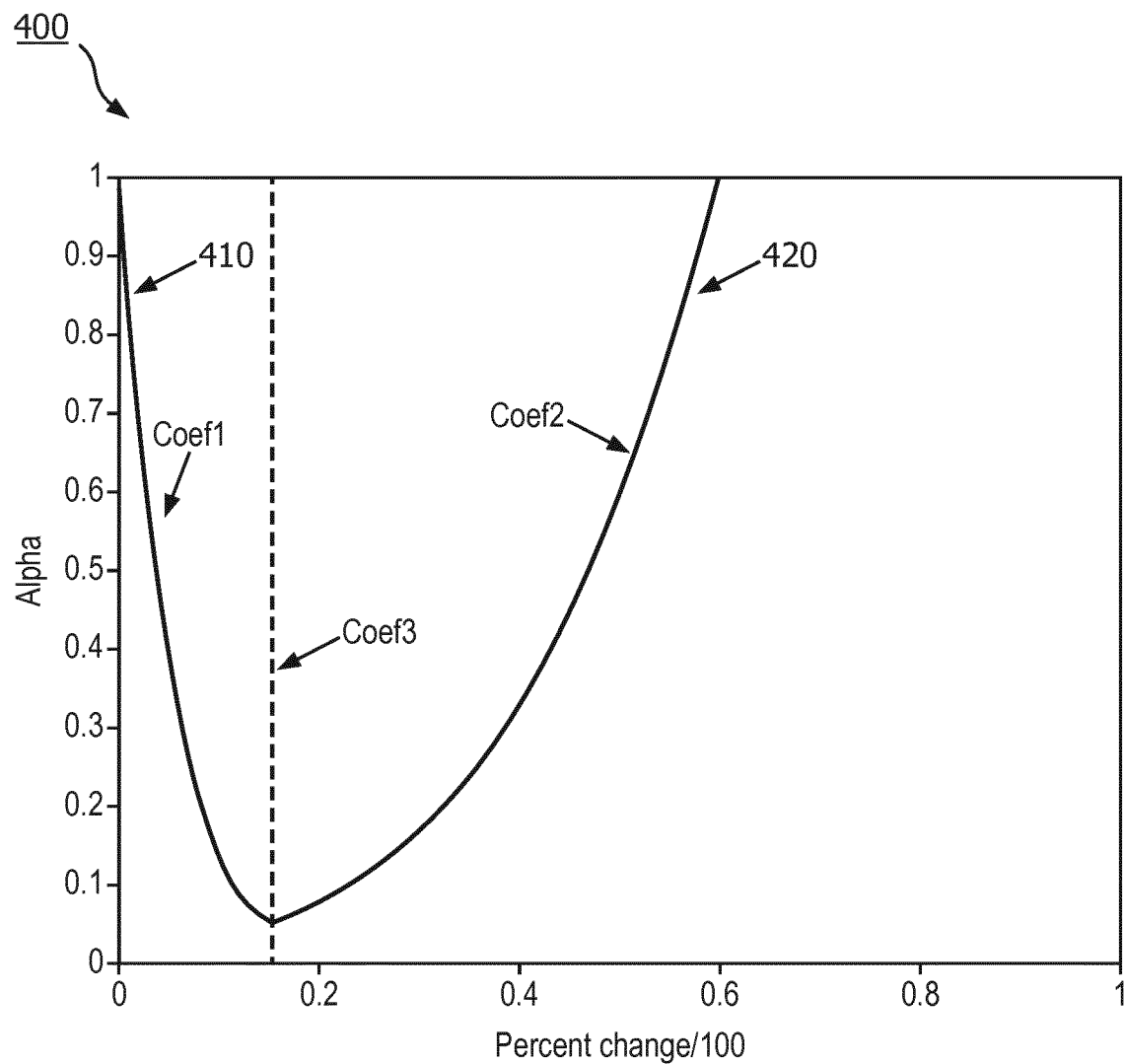
FIG. 4 is a plot of an example transfer function which may be used by a flash suppression processor to generate blending coefficients in accordance with some embodiments of the present disclosure.
Figure 5A:
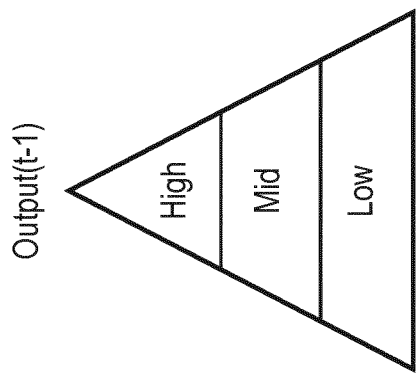
FIGS. 5A and 5B are pictorial representations of blending processes in accordance with some embodiments of the present disclosure.
Figure 5A:
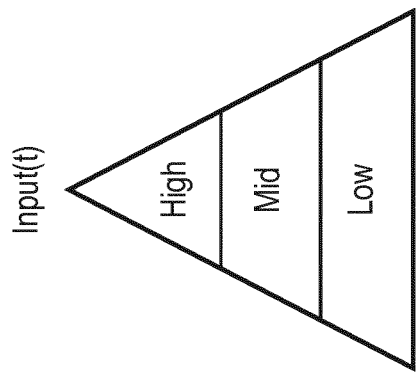
Figure 5A:
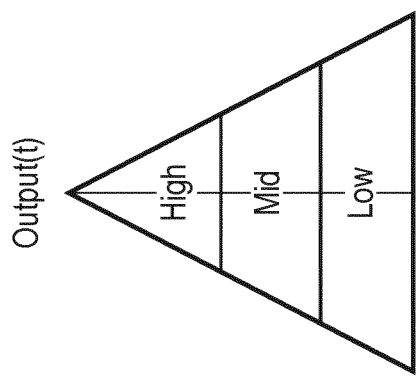

In one example, an alpha map may be generated by a transfer function as shown in FIG. 4. The transfer function 400 in FIG. 4 is a piecewise exponential function with an exponential decay and an exponential growth curve portions 410 and 420, respectively. The decay portion of the function in this example is designed as the portion that will reject tissue flash. A growth portion may be included in the transfer function to improve performance of the flash suppression processor. Experimental testing revealed that large, continuous flash artifacts that arise due to transducer motion may be treated as cardiac flash by the flash suppression processor and could thus be continuously suppressed, which may result in image 'freezing' if the transducer is moved continuously. To avoid image "freezing" an exponential growth curve may be added to relax the suppression effect due to transducer motion. The transfer function (also referred to herein as Alpha transfer function) may be defined by the following equations:

$$\text{Decay} = \exp(-1 * \text{coef1} * x) \quad \text{(eq. 1)},$$

$$\text{Growth} = \text{pow}(x + \text{coef3}, \text{coef2}) \quad \text{(eq. 2), and}$$

$$\text{Alpha} = \min(\max(\text{Decay}, \text{Growth}), 1.0) \quad \text{(eq. 3)},$$

where x is the FractionalChange. According to this definition, Decay represents the decay portion 410 of the function (i.e., the downward trending curve) and is governed by coef1 which determines the rate of exponential decay. Growth is the growth portion 420 (i.e., the upward trending portion of the curve) and is governed by coef3, which shifts the curve left or right, and coef2, which controls the rate of exponential growth. The coefficients coef3 in the illustrated example is set to 0.4 and coef2 is set to 5, while coef1 may be determined by optimization, e.g., in accordance with the principle that the higher the coef1 is the more quickly it penalizes tissue flash. The coef2 and coef3 may be set to other values in different embodiments of the present disclosure. Also, a variety of other transfer functions may be used, such as a linear parabolic transfer function, to map the signal strength change values to alpha values. The alpha values are provided to a blending processor 320 which generates the compensated output frame 313-3 (e.g., output t, in this example). The Output frame may be generated in accordance with the following equation:

$$\text{Output}(t) = \text{Alpha} * (\text{Input}(t)) + (1 - \text{Alpha}) * \text{Output}(t-1) \quad \text{(eq. 4)},$$

which may also be referred to as an alpha blend equation which blends the current frame with the previous frame based on the Alpha value. The alpha blend equation is also pictorially represented in FIG. 5A. The pyramidal structure associated with each frame represents the different spatial frequencies that may make up any given image frame. Blood flow from small vessels would be located in the high spatial frequency area (i.e., toward the top of the pyramidal structure), while tissue flash would be located in the low spatial frequency region (i.e., towards the bottom of the pyramidal structure). Thus, the assumption made here is that unwanted flash (i.e., tissue clutter), whether it is cardiac or otherwise, is of low spatial frequency, and therefore by subtracting out low spatial frequency change between frames flash artifacts would be suppressed. While the alpha value is computed from the low spatial frequency portion of the image, the blend is evenly applied to all spatial frequencies in the image. In some embodiments, performance may be improved by a thresholding step. In some embodiments, the flash suppression unit 300 may additionally optionally include a comparator block which compares the average power of Input t a power threshold. If the average power is higher than the threshold, then a global gain subtraction equivalent to the difference is introduced.

As described above, the alpha blend equation applies a single persistence coefficient to blend the two frames and produce the blended or compensated frame. Performance of the flash suppression unit may be further enhanced by the use of two blending maps, e.g., as shown in FIG. 3B. The flash suppression processor 300' in FIG. 3B may include some or all of the same components of flash suppression unit 300 and may additionally include a beta blend component 319, which generates a beta blending map 318-2, e.g., to improve the performance of the flash suppression unit as will be further described. Experimental testing including live scanning reveals that a blending step that uses a single persistence coefficient (e.g., an alpha blend equation) may produce side effects such as a laggy feeling and/or blurred blood flow speckle, which may be undesirable. Additionally, the alpha blending map and alpha blend equation may not sufficiently address flash that arises due to transducer motion. To address one or more of these problems, an additional persistence coefficient may be computed and used in the blending process.

Figure 5B:
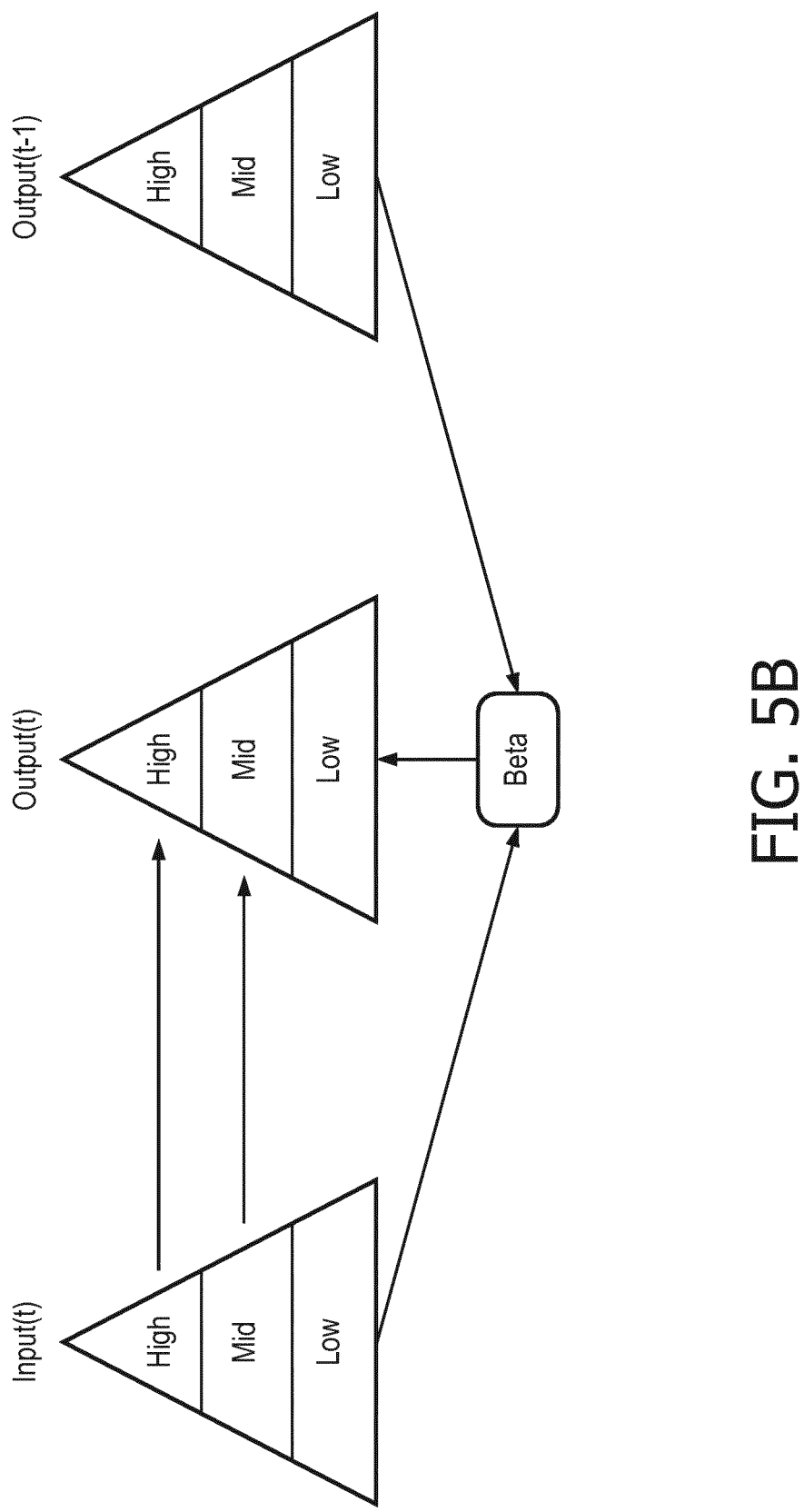

As shown in FIG. 3B, a beta blending map may be generated in accordance with the following equation:

$$\text{Beta} = \text{ScalingFactor} * (\Sigma \text{Input}(t)_L - 1 \Sigma \text{Output}(t-1)_L) \quad \text{(eq. 5)},$$

where Input$(t)_L$ is the low frequency component of the input frame, and Output$(t-1)_L$ is the low frequency component of the previous frame. Thus, the beta map may affect only the low frequency components of the image, based on the assumption that tissue flash is of low spatial frequency. This is pictorially represented in FIG. 5B. In the illustration in FIG. 5B, the different spatial frequencies are pictorially shown using pyramidal structures. Here, Beta values are calculated from low spatial frequency subbands. Output(t) is obtained from Input(t) except for the low frequencies, which is computed from the difference in low frequencies between Input(t) and Output(t-1) scaled by a scaling factor.

Referring again to FIG. 3B, blending unit 320' may produce an output using the alpha and beta blend values, in accordance with the following blend equation:

$$\text{Output}(t) = \text{Alpha} * (\text{Input}(t) - \text{Beta}) + (1 - \text{Alpha}) * \text{Output}(t-1) \quad \text{(eq. 6)},$$

where the Alpha values and Beta values are obtained from bloc318-1 and 318-2, respectively. Therefore, computing a difference between blurred frames Blur t and Blur t−1 (weighted by signal strength change), the Beta map is passed into the blend to enhance tissue flash suppression. In some embodiments, a system may use only Beta values for flash suppression. Also, while not shown in FIG. 3B, the flash suppression unit 300' may additionally, optionally include a comparator block 322 for performing power thresholding as previously described.

Figure 6:
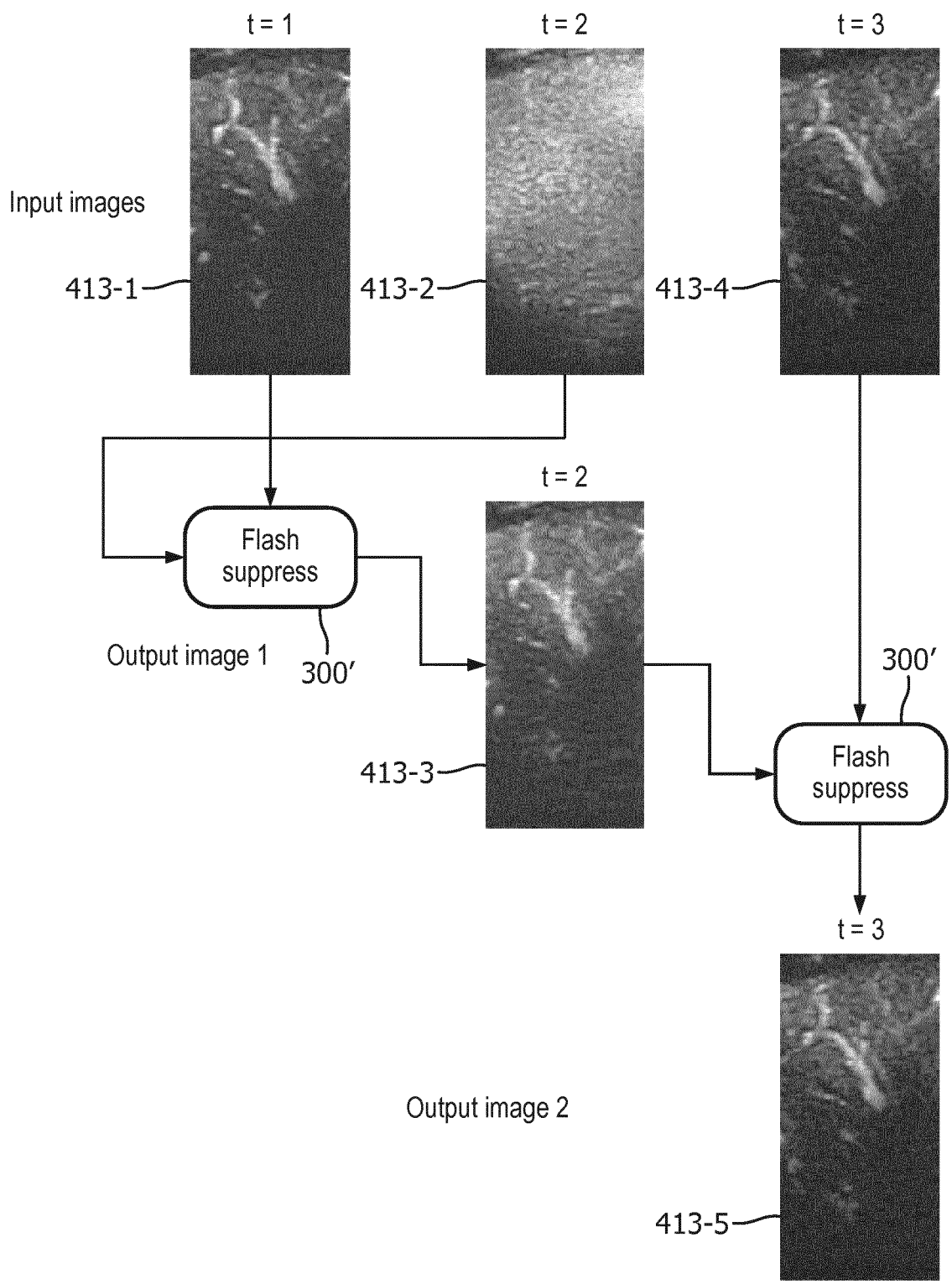
FIG. 6 is a sequence of input and output images associated with a flash suppression process in accordance with some embodiments of the present disclosure.

FIG. 6 shows an example set of input images and the resulting output images after undergoing the flash suppression in accordance with the examples herein. In the illustrated example, frames 413-1 and 413-2 are input frames into flash suppression unit 300', whereby regions of the image that experience large positive changes in intensity are suppressed by persisting data from the previous image, while regions with low or negative changes in intensity are not suppressed. The adjusted output frame 413-3 and the next frame 413-4 are then input through the flash suppression unit 330' to produce the next adjusted frame 414-5, and so on. This process is repeated for each subsequent frame, which may occur in real time, e.g., during real-time image data acquisition. Thus, as illustrated, a system including a flash suppression unit in accordance with any of the examples herein may be able to produce output images in which flash components in the image are suppressed while preserving flow information.

Referring back to the example in FIG. 2, additionally and optionally, the system may include a blending processor at the display generation stage (also referred to as display blending processor 242), which may be operable to smoothly blend B-mode (or echo) data and Doppler (e.g., power or velocity) data based on one or more Alpha blend values computed in accordance with the examples described further below. In addition, the blending processor at the display generation stage provides additional flash artifact suppression. For example, in addition to smoothly blending echo and flow data, this blending processor may also provide some additional artifact removal since bright echoes seen in B-mode are often a source of tissue flash. The blend at this stage may work to further suppress flash from these bright regions. In some embodiments, the display blending processor may include two blend stages including a difference blend and a log power blend. Combining these two blend stages may produce a more natural looking blended image. In other embodiments, the blending processor 242 may include only one blend stage (e.g., the difference blend or lob power blend stage), as described herein.

Difference Blend

Figure 8A:
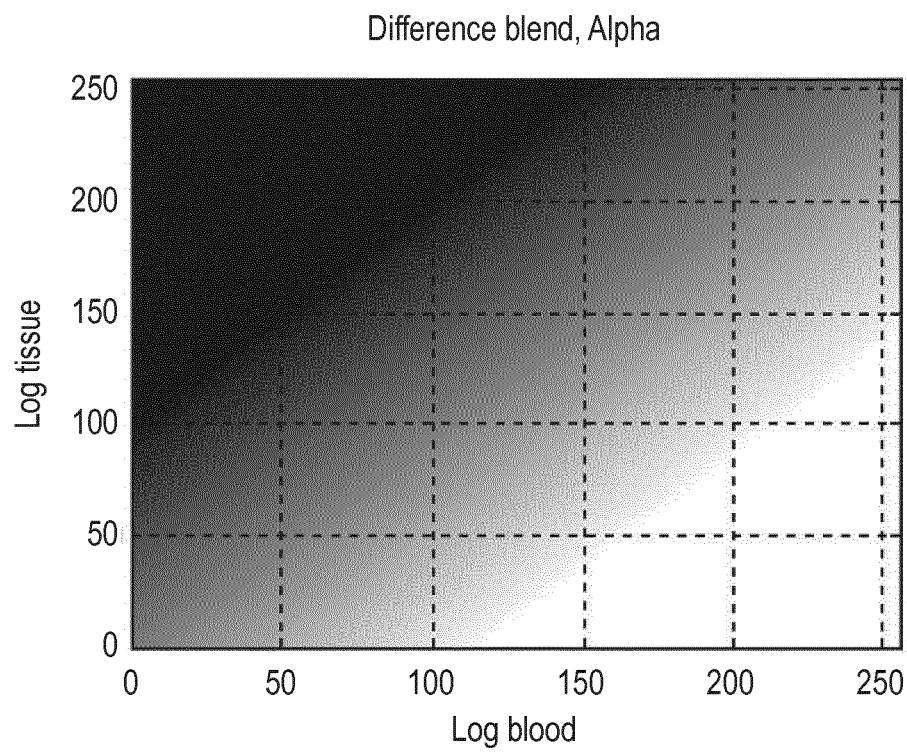
FIGS. 8A-8C are exemplary plots of blending coefficients and look-up tables for various blending stages of a display blending process in accordance with some embodiments of the present disclosure.
Figure 8A:
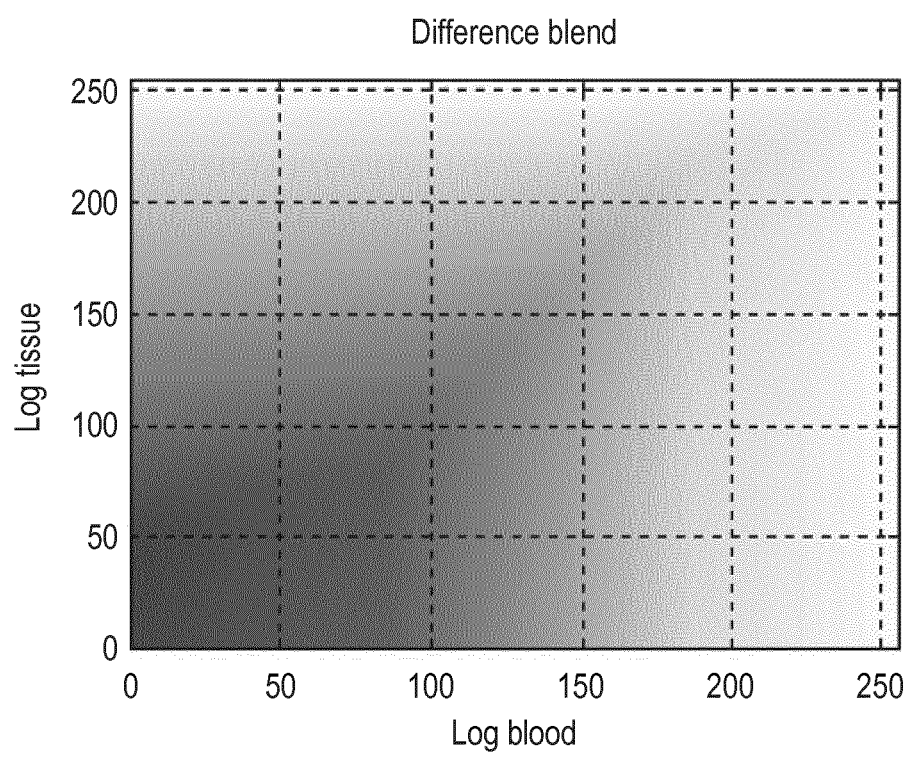

During a difference blend, the display blending processor 242 evaluates the difference between the log power of color or power signal and the log power of the echo signal and then computes the blend level based on that difference, e.g., in accordance with the following equation:

$$\text{Alpha1} = \min[\max[(\text{ColorPowerVel} - \text{Echo} + \text{Offset}) * \text{Slope}, 0], 255] \quad (\text{eq. 7}),$$

where ColorPowerVel is the value of the power/velocity data (in log units) and echo is the value of the echo data (in log units). Offset controls the hinge-point on which the blend occurs (in terms of differences in signal strength between flow/power and echo) and Slope determines the rapidity that the blend occurs and the range (in difference values) that the blend occurs. In preferred embodiments, write priority may be applied. That is, if the echo signal value is large compared to the power/flow signal, then priority will be given to the echo data to be displayed. On the contrary, if the power/flow signal is large compared to the echo signal value, then the blend will be dominated by the flow signal data. Additionally, using this method of blending will help suppress color on bright target artifacts as it is typically a highly echogenic reflector that causes the color artifact. Therefore, a strong echo reflector will push the blend to hide the flow signal. FIG. 8A shows example Alpha1 values and a resulting 2D look up table (LUT) for using the difference blend component. Notably, at low log blood values, the alpha values are not necessarily near zero which leads to a blend that has blood flow colors even at very low flow values.

Log Power Blend

Figure 8B:
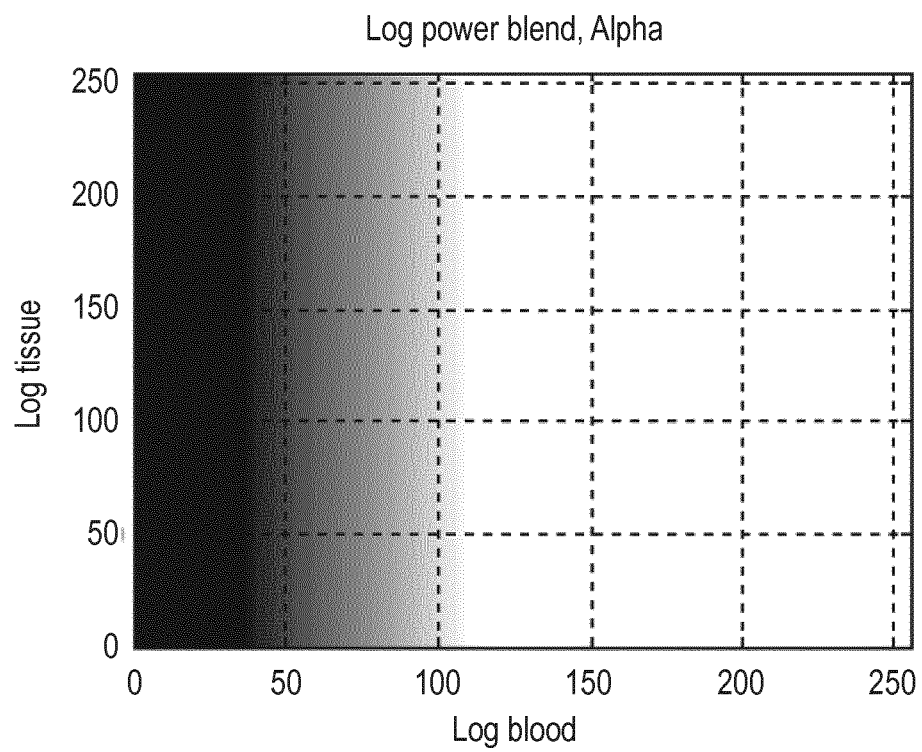
Figure 8B:
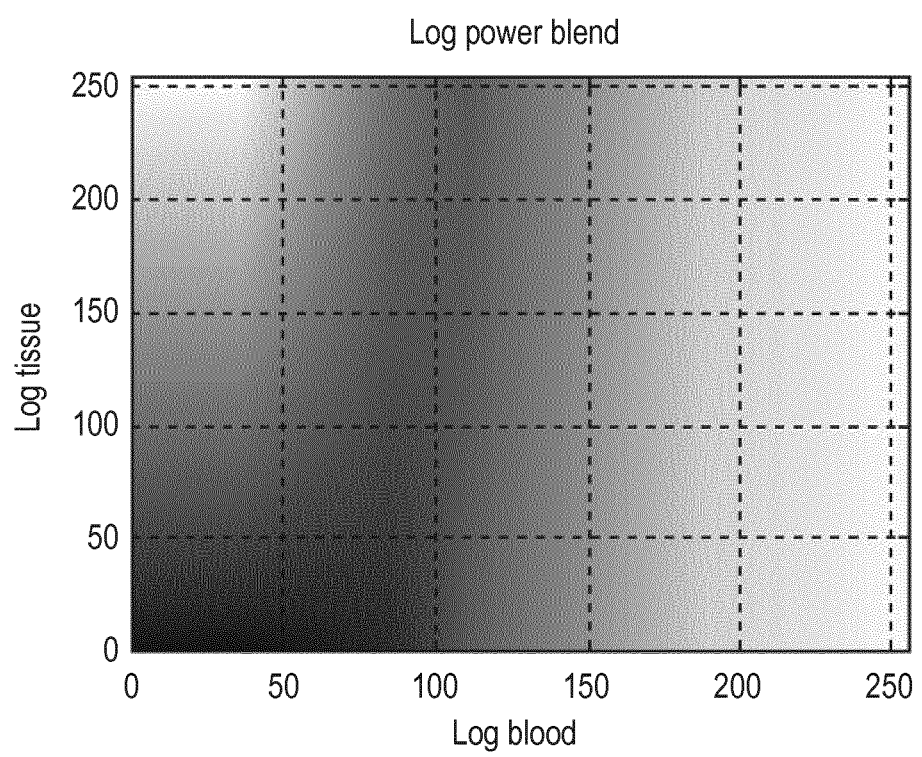

The second component of the blend is a log power blend based on the flow signal strength:

$$\text{Alpha2} = \min[\max[(\text{ColorPowerVel} - \text{Offset2}) * \text{Slope2}, 0], 255] \quad (\text{eq. 8}),$$

where ColorPowerVel again is the value of the power/velocity data (in log units). Offset2 controls essentially the hinge-point on when the blend occurs and Slope2 determines the rapidity that the blend occurs and the range (in difference values) that the blend occurs. That is during a log power blend, the display blending processor 242 looks only at the color or power signal component without taking into effect the echo signal. FIG. 8B shows example Alpha2 values and a resulting 2D look up table (LUT) for using the log power blend component. Notably, even at low log blood values the blend will show echo values.

Combined Alpha and Blending Process

As described, in some embodiments, the display blending processor 242 may include both blend stages and in such cases, the display blending processor 242 may obtain a combined alpha value, e.g., in accordance with the following equation:

$$\text{Alpha} = (\text{Alpha1}/255) * (\text{Alpha2}/255) \quad (\text{eq. 8}).$$

By the use of the second blending stage and its resulting Alpha blend value, the two stage blending process may provide an improved blending control at low flow/power values. That is, at small colorPowerVel, the combined blending value Alpha will largely be dominated towards grayscale since Alpha2 will be very small. At larger colorPowerVel values, Alpha will be determined largely by Alpha1. In other embodiments, a weighting factor may be applied in combining the alpha values from the two blend stages.

A combined blend may then be performed by the display blending processor 242 on anti-logged echo and colorPower data in accordance with the following equation:

$$\text{FinalOutput} = \log 2(\text{anti log } 2(\text{ColorPowerVel}) * \text{Alpha} + \text{anti log } 2(\text{echo}) * (1 - \text{Alpha}))$$

Figure 8C:
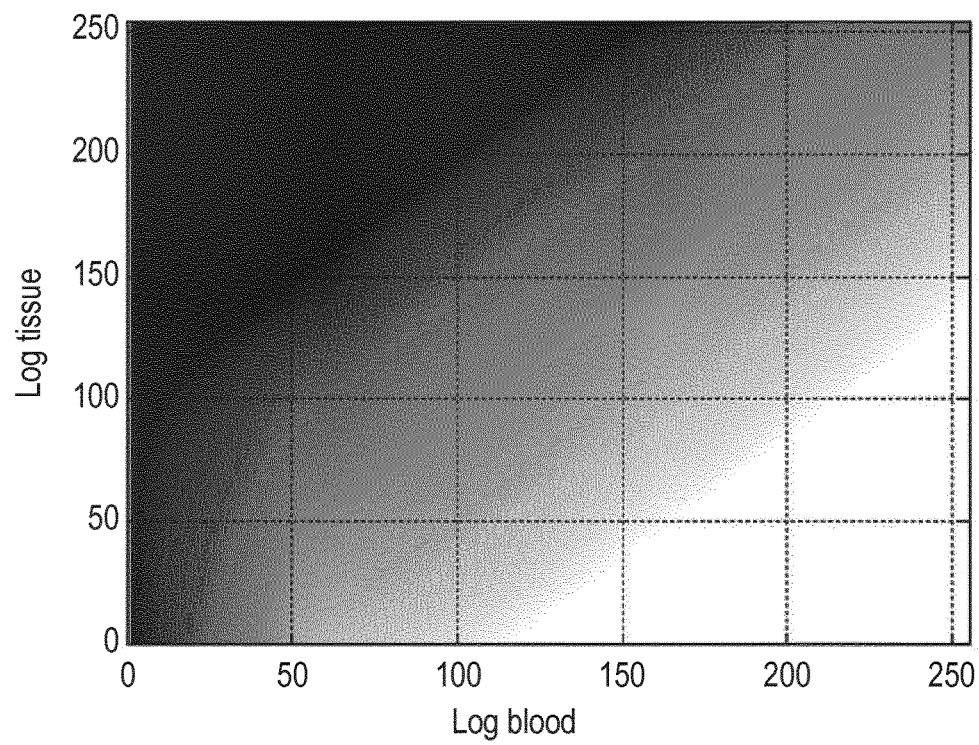
Figure 8C:
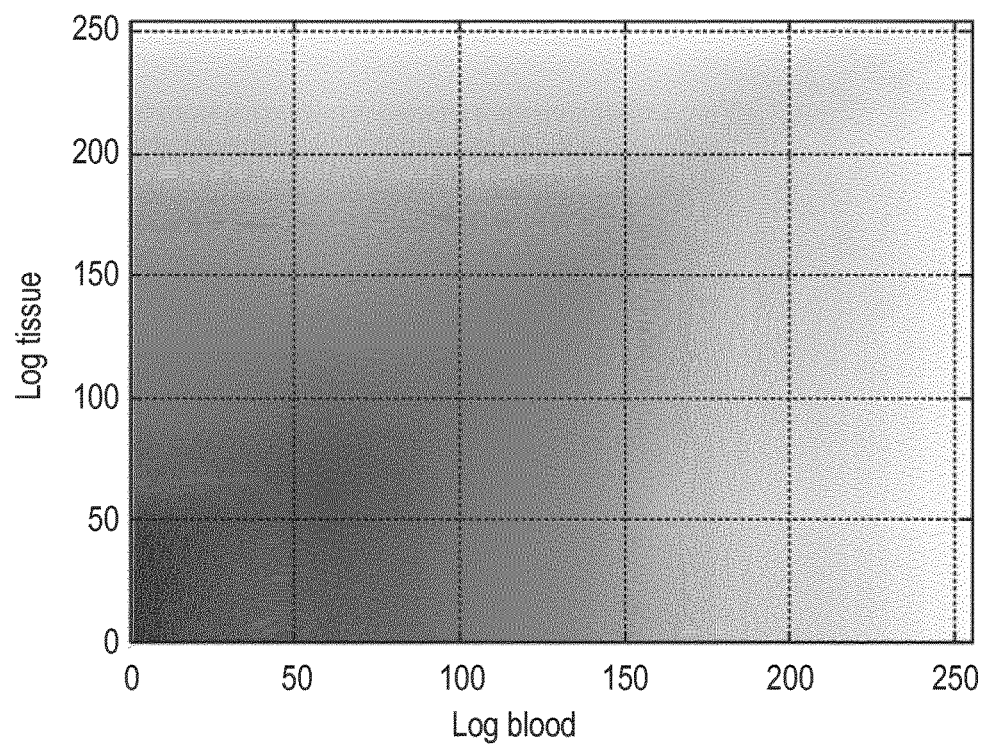

A blend using the above equation may provide a generally more natural blended output as compared to blending using only one of the two components or conventional techniques; although it is envision that for simplicity some systems may not include both blending components. FIG. 8C shows example Alpha values and a resulting 2D look up table (LUT) for using the combined blending process. As shown, the combined blended process may provide the benefit of writing echo data at very low flow values while retaining the comparison approach of the difference blend at larger blood values. While this two-stage blending process may be employed in some embodiments, in other embodiments according to the present disclosure, the system may employ components for improved flash suppression without using the two-stage blending process (e.g., using conventional display blending techniques). Generally, any of the examples herein may be used in combination with any other example of the present disclosure regardless of whether the specific combination was expressly illustrated or discussed.

Figure 7:
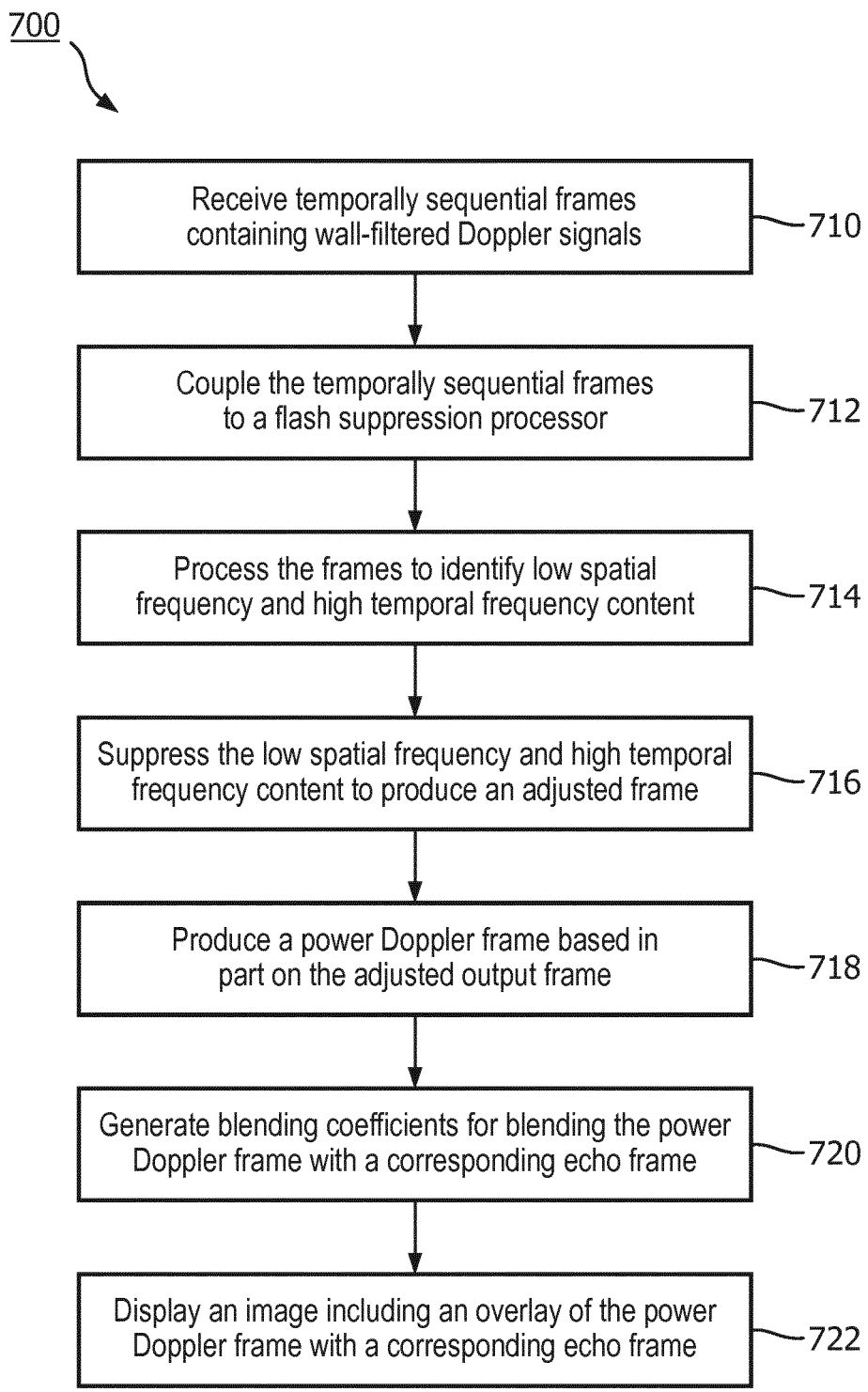
FIG. 7 is a flow diagram of a process for power Doppler imaging in accordance with some embodiments of the present disclosure.

FIG. 7 shows a flow diagram of an example process for power Doppler imaging in accordance with the present disclosure. The process 700 may include receiving temporally sequential frames (e.g., two or more frames) of wall-filtered Doppler signals, as shown in block 710. In some embodiments, the additional cutter suppression may be performed using two temporally sequential frames (e.g., temporally consecutive or temporally sequential but spaced by intervening one or more frames) as input. In other embodiments, the additional cutter suppression may be performed using more than two sequential frames as input. In preferred embodiments, at least one of the input frames may be a previously adjusted frame so as to provide an infinite impulse response (IIR) filter. Each input frame may contain Doppler signals after the signals have been filtered through a conventional wall filter that is typically used as part of the Doppler processor (i.e., to isolate blood flow from tissue). However, as discussed, the wall filter may not be sufficient to remove all tissue clutter particularly in low flow applications. Depending on the imaging mode, the Doppler signals may be further processed within the Doppler processor, along either one of two paths, one configured for extracting flow information for the generation of colorflow Doppler images and one associated with extracting power information for generating power Doppler images. Thus, additionally, and prior to providing the wall-filtered Doppler signals to the clutter or flash suppression processor, the Doppler signals may be processed to estimate the power or intensity of the signal and it is the power signals (rather than the velocity/flow information) that are then coupled to the clutter or flash suppression processor, as shown in block 712.

The temporally sequential frames of Doppler signals are then processed in accordance with any of the embodiments of the present disclosure to identify, as shown in block 714, low spatial frequency and high temporal frequency content, which may be indicative of tissue clutter (e.g., as illustrated in Table 1). As further shown in block 716, the low spatial frequency and high temporal frequency content is suppressed to produce an adjusted output frame. Power Doppler image frames can then be generated from power Doppler frames that include at least the adjusted output frame, e.g., as shown in block 718.

In some embodiments, the processing of the temporally sequential frames to identify low spatial frequency and high temporal frequency content may involve passing each of the temporally sequential frames through a spatial low-pass filter (e.g., a boxcar filter or any other type of spatial low-pass filter) and then passing the spatially filtered frames (also referred to as blurred frames) through a temporal high-pass filter to identify rapidly changing content between the frames. In some embodiments, temporal high-pass filtering may be accomplished in accordance with a variety of techniques such as by using a transfer function that is responsive to the change from frame to frame. For example, a weighted sum of the frames may be used to identify high temporal frequency content from the blurred frames, which can then be used to adjust the output frame (e.g., by adjusting a gain, generating blending coefficients, or other adjustment method for suppressing the identified low spatial frequency and high temporal frequency content. Thereby, in embodiments herein, at the output of the filtering operation the low spatial frequency and high temporal frequency content will be identified and adjustment parameters (e.g., a gain adjustment, a blending coefficient, or other) may be computed for suppressing the low spatial frequency and high temporal frequency content from at least one of the temporally sequential frames (e.g., a current input frame). The adjustment parameter(s) may be applied to the at least one of the temporally sequential frames (e.g., a current input frame) to produce one or more adjusted frames and to subsequently produce power Doppler images based on the adjusted frame(s).

In some embodiments, the temporal responsiveness between the filtered frames (e.g., rapid temporal variations between the blurred sequential frames) may be determined by computing a change (for example, a percentage change or a fractional change, or simply a signal strength difference) in signal strength between the filtered frames. This calculation may be performed at every pixel (for 2D frames) or voxel (for 3D frames) in the frames. Blending coefficients based on the computed changes in signal strength may be generated. Blending coefficients or other adjustment parameters may be obtained, for example, based on a computed percent, fractional, or difference change in signal strength, which in some embodiments may be achieved using a variety of transfer functions. In one specific described example, a transfer function having a decay component and a growth component is used; however, the embodiments of the present disclosure are not limited to that specific illustrated example. In some embodiments, the method may further include generating second blending coefficients, for example based on a difference of the signal strength between the filtered frames at every pixel or voxel in the frames, and the adjusting of the input frame may be performed further using the second blending coefficients. As implied, the techniques described herein can be equally applicable to two-dimensional (2D) data sets, e.g., pixel-by-pixel processing of 2D image frames, or it may be applied to three-dimensional (3D) data set, such as by performing the clutter suppression on 3D data frames. In some embodiments, the steps of the process may be performed in real time, i.e., during the acquisition of one or more of the temporally sequential frames.

In some embodiments, instead of using blending coefficients, the signal strength may be directly adjusted based on the computed change, for example by adjusting a gain, or by weighting, or other suitable adjustment to suppress the low spatial frequency and high temporal frequency content from the input frames and to produce an adjusted output frame. Power Doppler image frames may then be generated using at least one adjusted output frame, e.g., as shown in block 718.

The process 700 may further include generating and displaying ultrasound images including the power Doppler information from the adjusted output frame (e.g., an adjusted CPA frame) and corresponding echo information. When generating the image for display, the process may optionally include a blending step in which the adjusted output frame is blended with a corresponding echo frame to produce the power Doppler image. Thus, in some embodiments, the method may further include, as shown in blocks 720 and 722, blending the adjusted output frame with a corresponding echo frame to produce the power Doppler image (e.g., the combined or overlaid image in which the power Doppler frame is overlaid on the echo frame). The adjusted output frame may include signal power information and the corresponding echo frame may include echo intensity information, and in some embodiments the blending of the adjusted output frame with the corresponding echo frame may involve computing at least one blending coefficient using at least one of the signal power information or the echo intensity information from the respective frame. Any of the methods described herein may be embodied in non-transitory computer-readable medium comprising executable instructions and which when executed cause a processor (e.g., a processor of an ultrasound imaging system) to perform the method embodied therein.

The steps of the method may be repeated in real time while acquiring the ultrasound signals so as to provide real-time power Doppler images on a display of a medical imaging system. For each repetition in the sequence, the adjusted output frame is used together with a new input frame as inputs to the flash suppression process described herein, thereby providing an IIR type filtering process which utilizes the prior output as feedback and may thus provide improved performance over existing flash suppression techniques.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A method of power Doppler imaging comprising:
receiving a plurality of temporally sequential frames of wall-filtered power Doppler signals, wherein the plurality of temporally sequential frames includes at least one previously adjusted output frame;
adjusting at least one of the plurality of temporally sequential frames, wherein the adjusting includes:
filtering the plurality of temporally sequential frames to identify low spatial frequency and high temporal frequency content; and
suppressing the low spatial frequency and high temporal frequency content to produce an adjusted output frame; and
generating a power Doppler image based, at least in part, on the adjusted output frame.

2. The method of claim 1, wherein the adjusting at least one of the plurality of temporally sequential frames includes:
filtering each of the plurality of temporally sequential frames to remove high spatial frequency content from each of the temporally sequential frames and produce filtered frames having relatively low spatial frequency content;
determining the temporal responsiveness between the filtered frames for every spatial location in the frames; and
adjusting the at least one of the plurality of temporally sequential frame based on the temporal responsiveness between the filtered frames.

3. The method of claim 2, wherein the filtering each of the plurality of temporally sequential frames comprises passing each of the plurality of temporally sequential frames through a spatial low-pass filter.

4. The method of claim 3, wherein the spatial low-pass filter is a boxcar filter.

5. The method of claim 2, wherein determining the temporal responsiveness between the filtered frames includes:
computing a change in signal strength between the filtered frames for every pixel or voxel in the frames; and
generating blending coefficients based on the computed changes in signal strength.

6. The method of claim 5, wherein the generating blending coefficients includes mapping the computed changes for each pixel or voxel to respective blending coefficients using a transfer function.

7. The method of claim 5, wherein the blending coefficients comprise first blending coefficients computed based on a fractional change in signal strength, the method further comprising:
generating second blending coefficients based on a difference of the signal strength between the filtered frames at every pixel or voxel in the frames, and applying the second blending coefficients to the at least one of the plurality of temporally sequential frame to adjust the at least one of the plurality of temporally sequential frame.

8. The method of claim 1 further comprising blending the adjusted output frame with a corresponding echo frame to produce the power Doppler image.

9. The method of claim 8, wherein the adjusted output frame includes signal power information and wherein the corresponding echo frame includes echo intensity information, and wherein the blending the adjusted output frame with the corresponding echo frame includes computing at least one blending coefficient based on the at least one of the signal power information or the echo intensity information from the respective frame.

10. An ultrasound imaging system communicatively coupled to a source of ultrasound echoes, the system comprising:
a wall filter configured to produce wall filtered Doppler signals responsive to the ultrasound echoes; and
at least one processor configured to:
receive temporally sequential frames of the wall filtered Doppler signals, wherein the two temporally sequential frames include at least one previously adjusted output frame;
filter the temporally sequential frames to identify low spatial frequency and high temporal frequency content;
suppress the low spatial frequency and high temporal frequency content to produce an adjusted output frame; and
generate power Doppler image data based, at least in part, on the adjusted output frame.

11. The ultrasound imaging system of claim 10, wherein the at least one processor includes at least one spatial low-pass filter configured to remove high spatial frequency information from the temporally sequential frames to produce blurred frames, and wherein the at least one processor is configured to generate one or more adjustment parameters based, at least in part, on the temporal responsiveness of the blurred frames.

12. The ultrasound imaging system of claim 11, wherein the processor is configured to calculate a change in signal strength between the temporally sequential frames for all pixels or voxels in the respective frames, and wherein the one or more adjustment parameters include blending coefficients based at least in part on the based on the calculated changes in signal strength.

13. The ultrasound imaging system of claim 11, wherein the at least one processor is configured to pass the calculated changes in signal strength through a transfer function to generate the blending coefficients, and wherein the transfer function comprises a decay component and a growth component.

14. The ultrasound imaging system of claim 11, wherein the blending coefficients are first blending coefficients generated based on a fractional change in signal strength, and wherein the at least one processor is further configured to:
generate second blending coefficients based on a difference of the signal strength between the two temporally sequential frames; and
adjust the current input frame further based on the second blending coefficients.

15. The ultrasound imaging system of claim 10, wherein the at least one processor is further configured to blend the adjusted output frame with a corresponding echo frame to produce the power Doppler image data.

* * * * *